United States Patent
Lampropoulos et al.

(10) Patent No.: US 10,702,281 B2
(45) Date of Patent: Jul. 7, 2020

(54) INFLATABLE RADIAL ARTERY COMPRESSION DEVICE

(71) Applicant: Merit Medical Systems, Inc., South Jordan, UT (US)

(72) Inventors: Fred Lampropoulos, Salt Lake City, UT (US); Blaine Johnson, Riverton, UT (US); Tyler Rees, Draper, UT (US); Kenneth Sykes, Bluffdale, UT (US); Randy Boyd, Riverton, UT (US); Tamara L. Newren, Saratoga Springs, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 131 days.

(21) Appl. No.: 15/648,110

(22) Filed: Jul. 12, 2017

(65) Prior Publication Data
US 2018/0014832 A1    Jan. 18, 2018

Related U.S. Application Data

(60) Provisional application No. 62/363,695, filed on Jul. 18, 2016.

(51) Int. Cl.
*A61B 17/122* (2006.01)
*A61B 17/135* (2006.01)
(Continued)

(52) U.S. Cl.
CPC ........ *A61B 17/135* (2013.01); *A61B 17/1325* (2013.01); *A61B 17/1355* (2013.01);
(Continued)

(58) Field of Classification Search
CPC .............. A61B 17/135; A61B 17/1325; A61B 17/1355; A61B 2017/00119;
(Continued)

(56) References Cited

U.S. PATENT DOCUMENTS

| 1,281,653 A | 10/1918 | Plummer |
| 2,332,107 A | 10/1943 | Nieburgs |

(Continued)

FOREIGN PATENT DOCUMENTS

| CN | 201205292 | 3/2009 |
| CN | 201861701 | 6/2011 |

(Continued)

OTHER PUBLICATIONS

International Search Report and Written Opinion dated Nov. 28, 2017 for PCT/US2017/041726.

(Continued)

*Primary Examiner* — Erich G Herbermann
(74) *Attorney, Agent, or Firm* — Stoel Rives LLP

(57) ABSTRACT

Radial artery compression devices with an inflatable chamber and a substantially rigid frame are disclosed. The inflatable chamber of the radial artery compression devices can be inflated and then deflated according to a predetermined protocol. Some substantially rigid frames can form a wall of the inflatable chamber. Some substantially rigid frames can include indicia to facilitate positioning of the inflatable chamber relative to a puncture site of a patient.

17 Claims, 7 Drawing Sheets

(51) Int. Cl.
*A61B 17/132* (2006.01)
*A61B 17/00* (2006.01)
(52) U.S. Cl.
CPC .............. *A61B 2017/00119* (2013.01); *A61B 2017/00199* (2013.01); *A61B 2017/00221* (2013.01); *A61B 2017/00442* (2013.01); *A61B 2017/00544* (2013.01); *A61B 2017/00734* (2013.01); *A61B 2017/00907* (2013.01)
(58) Field of Classification Search
CPC ........... A61B 2017/00221; A61B 2017/00442; A61B 2017/00544; A61B 2017/00734; A61B 2017/00907; A61B 17/12; A61B 5/02233; A61F 2013/00468; A61F 2013/0028
See application file for complete search history.

(56) References Cited

U.S. PATENT DOCUMENTS

| | | | |
|---|---|---|---|
| 3,050,064 | A | 8/1962 | Moore et al. |
| 3,376,846 | A | 4/1968 | Sekigushi et al. |
| 4,307,799 | A | 12/1981 | Zouzaoulas |
| 4,479,495 | A | 10/1984 | Isaacson |
| 4,557,262 | A | 12/1985 | Snow |
| 5,139,512 | A | 8/1992 | Dreiling et al. |
| 5,269,803 | A | 12/1993 | Geary et al. |
| 5,304,186 | A | 4/1994 | Semler et al. |
| 5,304,201 | A | 4/1994 | Rice |
| 5,613,491 | A | 3/1997 | Kanner et al. |
| 5,728,120 | A | 3/1998 | Shani et al. |
| 5,779,657 | A | 7/1998 | Daneshvar |
| 5,997,564 | A | 12/1999 | Shehata et al. |
| 6,068,646 | A | 5/2000 | Lam |
| 6,833,001 | B1 | 12/2004 | Chao |
| 7,758,574 | B2 | 7/2010 | Hijii et al. |
| 7,780,612 | B2 | 8/2010 | Ross |
| 8,147,417 | B2 | 4/2012 | Gavriely |
| 8,632,840 | B2 | 1/2014 | Avitable |
| 8,845,680 | B2 | 9/2014 | Lampropoulos et al. |
| 9,332,994 | B2 | 5/2016 | Pancholy et al. |
| 10,172,625 | B2 | 1/2019 | Wada et al. |
| 10,492,797 | B2 | 12/2019 | Okamura |
| 2002/0188315 | A1* | 12/2002 | Guzman ............... A61B 17/135 606/203 |
| 2003/0055453 | A1 | 3/2003 | Akerfeldt |
| 2005/0113866 | A1 | 5/2005 | Heinz et al. |
| 2005/0125025 | A1 | 6/2005 | Rioux |
| 2006/0058841 | A1 | 3/2006 | Mills et al. |
| 2007/0239092 | A1 | 10/2007 | Ross |
| 2007/0248810 | A1 | 10/2007 | McGee et al. |
| 2009/0209896 | A1 | 8/2009 | Selevan |
| 2009/0281565 | A1 | 11/2009 | McNeese |
| 2010/0211000 | A1 | 8/2010 | Killion et al. |
| 2010/0217202 | A1 | 8/2010 | Clark |
| 2010/0280541 | A1 | 11/2010 | Lampropoulos |
| 2012/0221041 | A1 | 8/2012 | Hansson et al. |
| 2012/0238934 | A1 | 9/2012 | During |
| 2012/0296369 | A1 | 11/2012 | Atthoff et al. |
| 2013/0079723 | A1 | 3/2013 | Andino et al. |
| 2013/0237866 | A1* | 9/2013 | Cohen ............... A61B 17/1325 600/502 |
| 2013/0245675 | A1 | 9/2013 | Wada et al. |
| 2013/0289613 | A1 | 10/2013 | Wada et al. |
| 2014/0012120 | A1 | 1/2014 | Cohen et al. |
| 2014/0012313 | A1 | 1/2014 | Finkielsztien et al. |
| 2014/0125718 | A1 | 5/2014 | Morrision et al. |
| 2014/0288408 | A1 | 9/2014 | Deutsch |
| 2015/0018869 | A1 | 1/2015 | Benz et al. |
| 2015/0164436 | A1 | 6/2015 | Maron et al. |
| 2015/0201948 | A1* | 7/2015 | Kornowski ........ A61B 5/02042 606/203 |
| 2015/0314074 | A1 | 11/2015 | Howlett et al. |
| 2015/0327871 | A1* | 11/2015 | Fortson ............... A61B 17/135 606/202 |
| 2016/0058988 | A1 | 3/2016 | Kesten et al. |
| 2017/0007807 | A1 | 1/2017 | Weerakoon et al. |
| 2018/0000494 | A1 | 1/2018 | Wada et al. |
| 2018/0008281 | A1 | 1/2018 | Hazama |
| 2018/0008282 | A1 | 1/2018 | Hazama et al. |
| 2018/0008283 | A1 | 1/2018 | Hazama |
| 2018/0014832 | A1 | 1/2018 | Lampropoulos et al. |
| 2018/0028195 | A1 | 2/2018 | Benz et al. |
| 2018/0042615 | A1 | 2/2018 | Kimura et al. |
| 2018/0185032 | A1 | 7/2018 | Matsushita et al. |
| 2018/0250017 | A1 | 9/2018 | Matsushita et al. |
| 2018/0280008 | A1 | 10/2018 | Okamura |
| 2019/0021742 | A1 | 1/2019 | Hazama |
| 2019/0029693 | A1 | 1/2019 | Okamura |
| 2019/0046214 | A1 | 2/2019 | Hazama |
| 2019/0133602 | A1 | 5/2019 | Kiemeneij et al. |
| 2019/0133604 | A1 | 5/2019 | Maeda et al. |
| 2019/0133605 | A1 | 5/2019 | Hazama et al. |
| 2019/0133606 | A1 | 5/2019 | Hazama |
| 2019/0133607 | A1 | 5/2019 | Hazama |
| 2019/0150938 | A1 | 5/2019 | Hazama et al. |
| 2019/0314035 | A1 | 10/2019 | Hopkinson et al. |

FOREIGN PATENT DOCUMENTS

| | | |
|---|---|---|
| DE | 4006696 | 11/1990 |
| FR | 2828231 | 2/2003 |
| JP | 2012010823 | 1/2012 |
| JP | 2013111444 | 6/2013 |
| JP | 6211285 | 10/2014 |
| JP | 2014200308 | 10/2014 |
| JP | 6261368 | 8/2015 |
| JP | 2015150298 | 8/2015 |
| JP | 6389510 | 9/2015 |
| JP | 6261420 | 11/2015 |
| JP | 2015188608 | 11/2015 |
| JP | 2017000259 | 1/2017 |
| JP | 2017000260 | 1/2017 |
| JP | 2017047036 | 3/2017 |
| JP | 2018011798 | 1/2018 |
| JP | 2018011867 | 1/2018 |
| JP | 2018019927 | 2/2018 |
| JP | 2018033602 | 3/2018 |
| JP | 2018075257 | 5/2018 |
| JP | 2018171081 | 11/2018 |
| JP | 2019047956 | 3/2019 |
| JP | 2019058498 | 4/2019 |
| JP | 2019154915 | 9/2019 |
| JP | 2019166265 | 10/2019 |
| JP | 2019208953 | 12/2019 |
| JP | 2019216947 | 12/2019 |
| JP | 2019217130 | 12/2019 |
| JP | 2020014588 | 1/2020 |
| JP | 6667234 | 2/2020 |
| JP | 202018686 | 2/2020 |
| JP | 202022679 | 2/2020 |
| JP | 202039815 | 3/2020 |
| JP | 202039816 | 3/2020 |
| WO | 2004041313 | 5/2004 |
| WO | 2015141786 | 4/2017 |

OTHER PUBLICATIONS

Office Action dated Jan. 10, 2019 for U.S. Appl. No. 15/705,759.
European Search Report dated Sep. 7, 2017 for EP 09763115.4.
International Search Report dated Nov. 18, 2009 for PCT/US2009/042868.
MedPlus, Inc., Tourniquet (Radial Artery Compression Device), http://www.bikudo.com/product_search/details/187473/tourniquet_radial_artey_compression_device.html Nov. 24, 2009.
Notice of Allowance dated Jun. 9, 2014 for U.S. Appl. No. 13/741,046.
Notice of Allowance dated Oct. 16, 2012 for U.S. Appl. No. 12/435,227.
Office Action dated Feb. 14, 2014 for U.S. Appl. No. 13/741,046.
Office Action dated Mar. 2, 2011 for U.S. Appl. No. 12/349,405.
Office Action dated Mar. 5, 2013 for U.S. Appl. No. 13/741,046.
Office Action dated Jun. 6, 2016 for U.S. Appl. No. 14/033,177.

(56) References Cited

OTHER PUBLICATIONS

Office Action dated Jun. 28, 2011 for U.S. Appl. No. 12/349,405.
Office Action dated Aug. 17, 2012 for U.S. Appl. No. 12/349,405.
Office Action dated Nov. 3, 2015 for U.S. Appl. No. 14/033,177.
Office Action dated Dec. 8, 2011 for U.S. Appl. No. 12/349,405.
Office Action dated Dec. 27, 2016 for U.S. Appl. No. 14/033,177.
International Search Report and Written Opinion dated Apr. 2, 2019 for PCT/US2018/060089.
International Search Report and Written Opinion dated Dec. 26, 2017 for PCT/US2017/051715.
International Search Report and Written Opinion dated Jul. 30, 2019 for PCT/US2019/026785.
Office Action dated Sep. 6, 2019 for U.S. Appl. No. 15/705,759.
Pua, et al.,"Snuffbox" Distal Radial Access, J Vasc Intery Radiol, No. 29:44, 2018.
Zhou, et al.,Transient Ulnar Artery Compression Facitivates Transradial Access, Medicine, No. 95:48 ,2016.
European Search Report dated Feb. 27, 2020 for EP17851579.7.

* cited by examiner

INFLATABLE RADIAL ARTERY COMPRESSION DEVICE

RELATED APPLICATIONS

This application claims priority to U.S. Provisional Application No. 62/363,695, filed on Jul. 18, 2016 and titled, Inflatable Radial Artery Compression Device, which is hereby incorporated by reference in its entirety.

TECHNICAL FIELD

The present disclosure relates generally to the field of medical devices. More particularly, some embodiments relate to compression devices, including radial artery compression devices with an inflatable chamber.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Numerous medical procedures involve insertion of one or more elongate medical devices into the vasculature of a patient. Some of these interventional procedures involve delivery of a medical device through a radial artery of the patient. Achieving hemostasis during and/or after an interventional procedure that involves puncturing the radial artery may present certain challenges.

To facilitate hemostasis at the radial access site, pressure may be applied slightly upstream of the skin puncture site. Such pressure may prevent or reduce the leakage of blood from the arteriotomy site and promote hemostasis. Certain embodiments described herein facilitate the application of pressure to promote hemostasis at a radial access site.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities. Thus, two components may be coupled to each other even though they are not in direct contact with each other. For example, two components may be coupled to one another through an intermediate component. The phrase "attached to" refers to interactions between two or more entities which are in direct contact with each other and/or are separated from each other only by a fastener of any suitable variety (e.g., an adhesive). The phrase "fluid communication" is used in its ordinary sense, and is broad enough to refer to arrangements in which a fluid (e.g., a gas or a liquid) can flow from one element to another element when the elements are in fluid communication with each other.

The terms "proximal" and "distal" are opposite directional terms. For example, the distal end of a radial artery compression device or a component thereof is the end that is furthest from the attachment point of the arm of the patient during ordinary use of the device. The proximal end refers to the opposite end, or the end nearest the patient during ordinary use. When used as a directional term, the term "radial" refers to the direction pointing from the center of the arm or hand to the thumb-side portion of the arm or hand. The term "ulnar" refers to the opposite direction. The particular volumes recited herein refer to the volumes of fluid that are delivered from a syringe that holds the recited amount of fluid at atmospheric pressure. For example, an inflatable chamber has a capacity of 15 mL if it is capable of receiving 15 mL of air from a syringe that holds 15 mL of air at atmospheric pressure.

Figure 1:
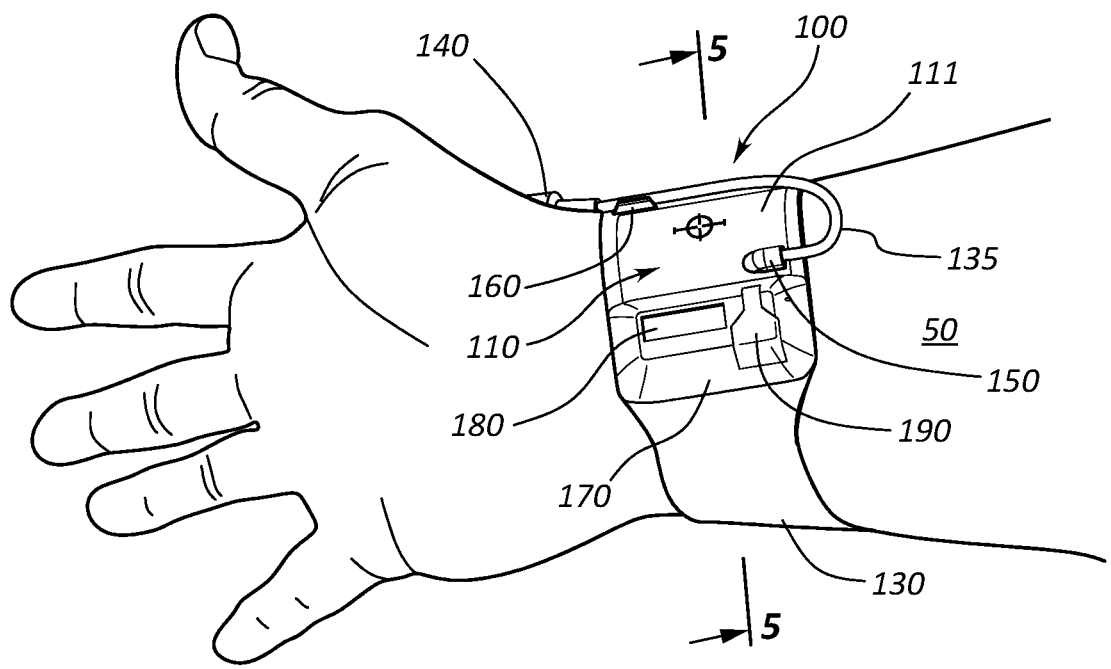
FIG. 1 depicts a radial artery compression device that is secured to a wrist of a patient.
Figure 2:
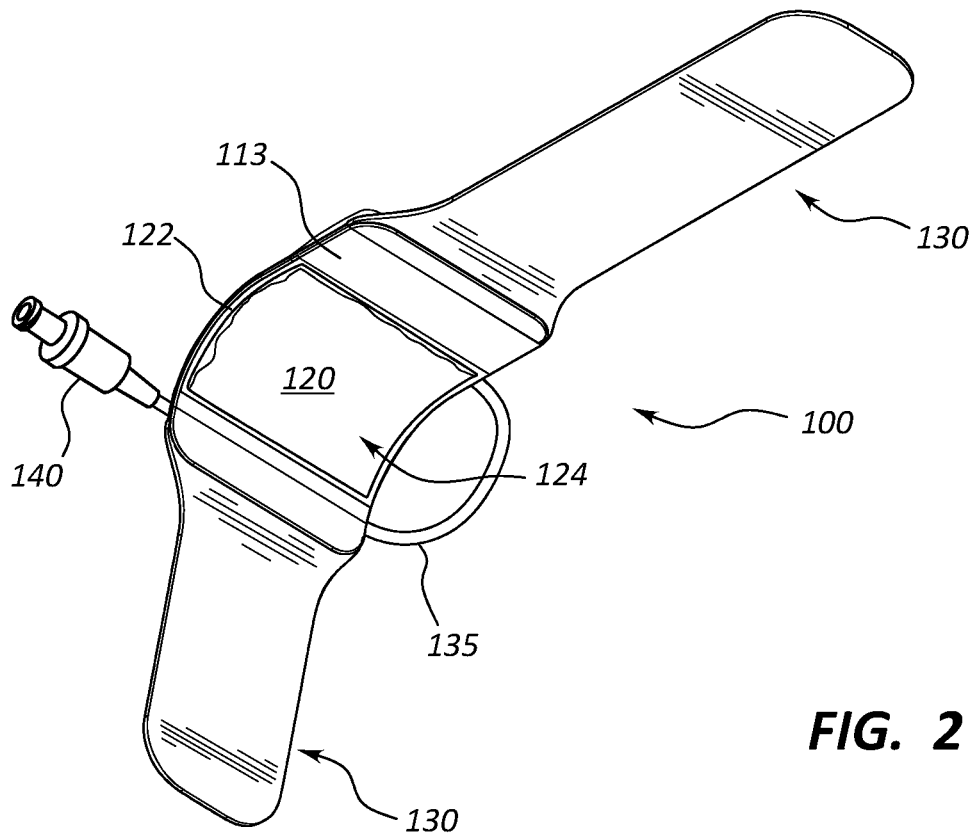
FIG. 2 is a perspective view of an underside of the radial artery compression device of FIG. 1.
Figure 3:
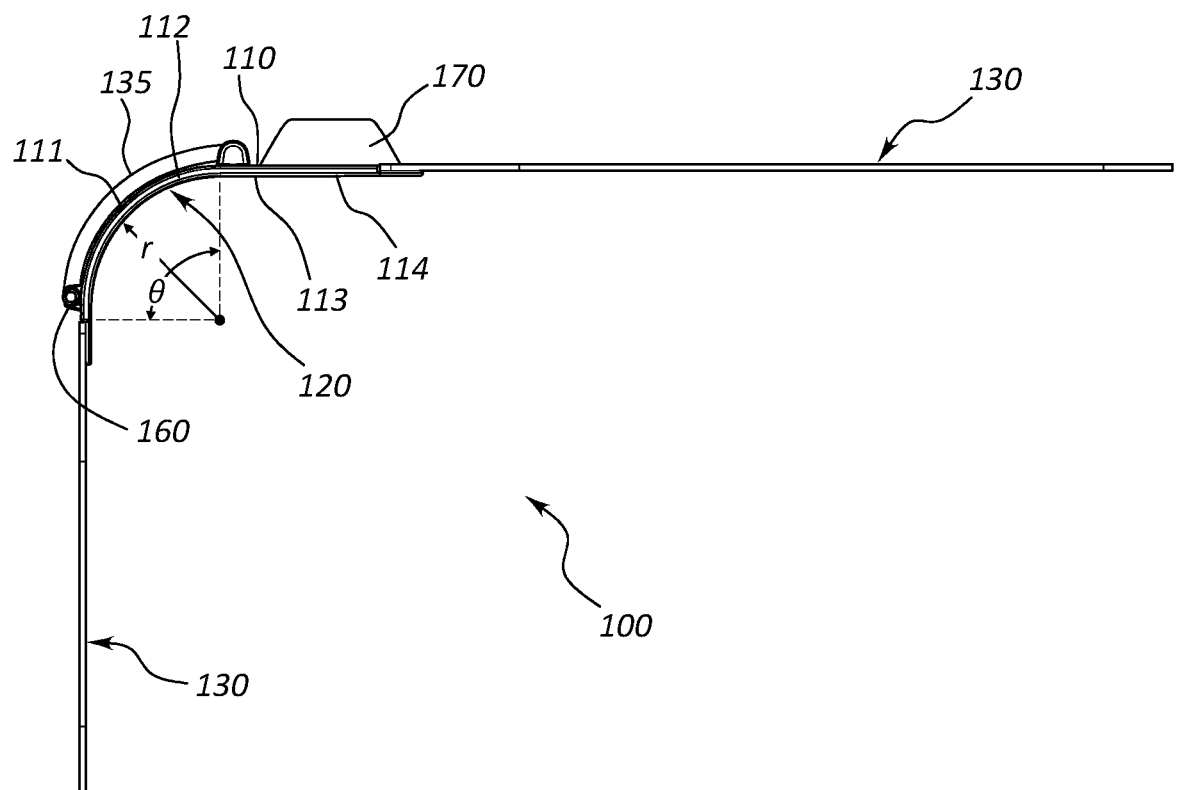
FIG. 3 is a side view of the radial artery compression device of FIGS. 1-2 with the inflatable chamber in an uninflated state.
Figure 4:
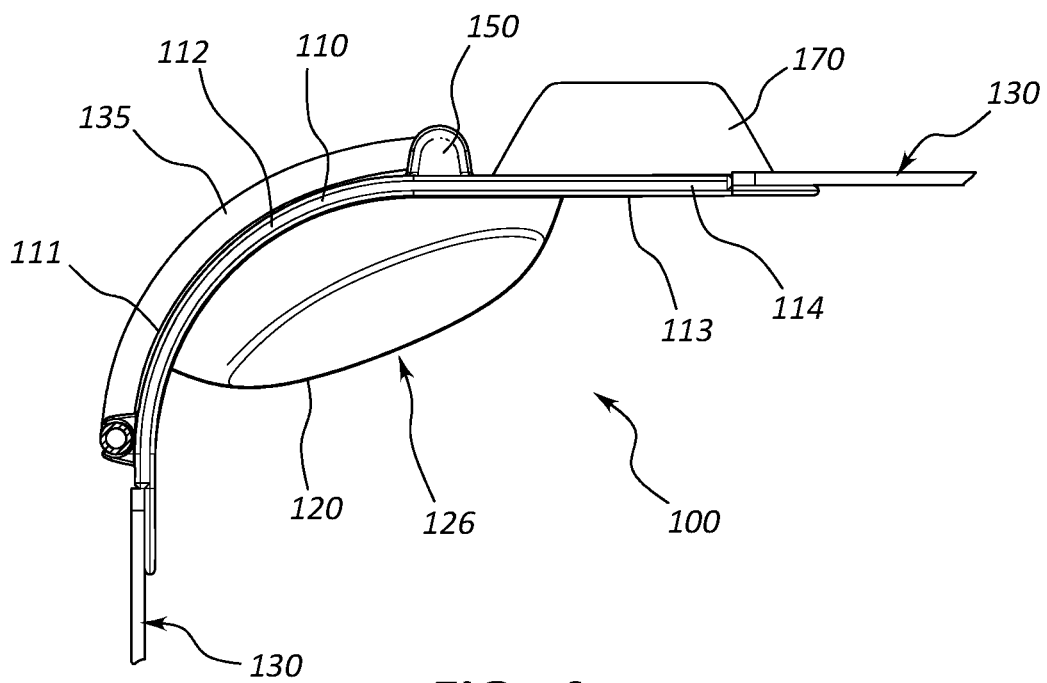
FIG. 4 is a side view of a portion of the radial artery compression device of FIGS. 1-3 with the inflatable chamber in a fully inflated state.
Figure 5:
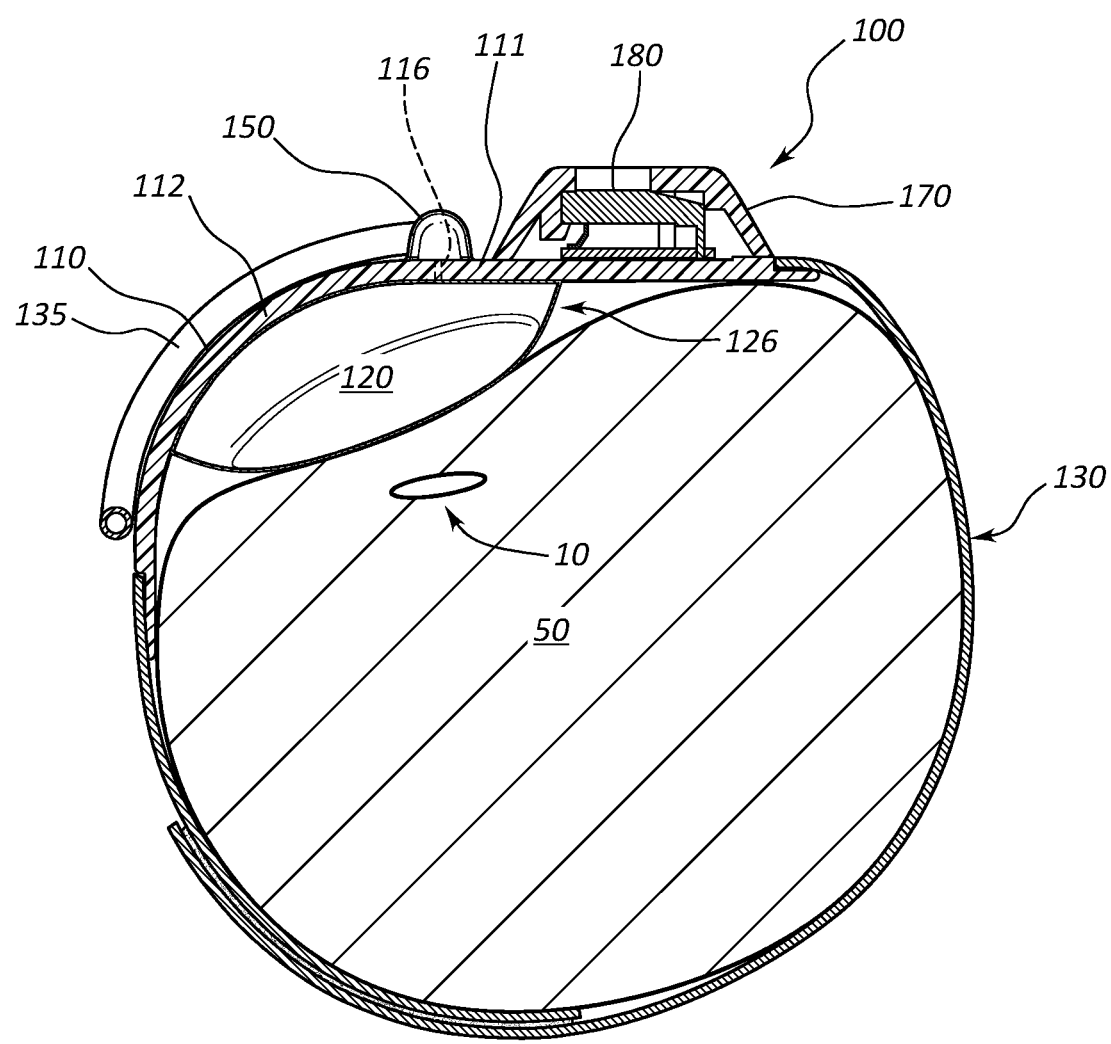
FIG. 5 is a cross-sectional side view of the radial artery compression device of FIGS. 1-4 around the wrist of a patient with the inflatable chamber in a fully inflated state.

FIGS. 1-5 provide alternative views of a radial artery compression device 100. More particularly, FIG. 1 depicts a radial artery compression device 100 secured to the wrist of a patient 50. FIG. 2 provides a perspective view of an underside of the radial artery compression device 100. FIG. 3 provides a side view of the radial artery compression device 100. FIG. 4 provides a side view of the radial artery compression device 100 with an inflatable chamber 126 in an inflated state. And FIG. 5 provides a side view of the radial artery compression device 100 on a wrist of a patient 50 with the inflatable chamber 126 in an inflated state.

As shown in FIGS. 1-5, the radial artery compression device 100 may include a substantially rigid frame 110, a flexible sheet 120, and a wristband 130.

The substantially rigid frame 110 may include an outer surface 111 and an inner surface 113. In some embodiments, the substantially rigid frame 100 is contoured to curve around a thumb-side portion of the wrist of the patient 50. For example, in some embodiments, the substantially rigid frame 110 includes a curved section 112 (see FIGS. 3-5). In the embodiment shown in FIGS. 1-5, the frame 110 is shaped as a curved (e.g., arched) sheet. The outer surface 111 of the frame 110 (or a portion thereof) may be convex, while the inner surface 113 of the frame 110 (or a portion thereof) may be concave. In some embodiments, the substantially rigid frame 110 further includes a substantially straight section 114 configured to be disposed adjacent an underside (i.e., a palmar side) of a wrist of the patient 50. In some embodiments, the substantially rigid frame 110 (or a portion thereof) is transparent.

In some embodiments, the curved section 112 may have a radius of curvature (r) of between 1.5 cm and 2.5 cm (see FIG. 3). Additionally or alternatively, the degree measure (θ) of an arc formed by the curved section 112 may be between 45 and 100 degrees. For example, in some embodiments, the curved section 112 is between 80 and 95 degrees (e.g., approximately 90 degrees).

The flexible sheet 120 may be coupled to the frame 110. For example, in some embodiments, the flexible sheet 120 includes a peripheral portion 122 that is attached to the frame 110 and a central portion 114 that is not attached to the frame 110. In some embodiments, the peripheral portion 122 of the flexible sheet 120 is attached to the frame 110 via welding or an adhesive. The flexible sheet 120 may be made from any suitable material, such as polyurethane or PVC. In some embodiments, the material of the flexible sheet is stretchable. In the depicted embodiment, the flexible sheet is substantially rectangular in shape, although other shapes are also within the scope of this disclosure. In some embodiments, the flexible sheet 120 (or a portion thereof) is transparent. For example, in some embodiments, both the substantially rigid frame 110 (or a portion thereof) and the flexible sheet 120 (or a portion thereof) are transparent, thereby allowing a practitioner to view a radial access site through the frame 110 and the flexible sheet 120. In some embodiments, the practitioner may need to view through only two layers (e.g., the frame 110 and the flexible sheet 120) to view the radial access site. Viewing through only two layers may provide improved visual clarity relative to embodiments in which the radial access site is viewed through more than two layers or parts.

The wristband 130 may be coupled to the frame 110. For example, the wristband 130 may include a first strap that is attached to one side of the frame 110 and a second strap that is attached to an opposite side of the frame 110. The wristband 130 may be configured to secure the frame 110 adjacent to the wrist of the patient 50. In some embodiments, the entire wristband 130 (or a portion thereof) is opaque. In some embodiments, the wristband 130 is colored and/or decorated. In some embodiments, the wristband 130 includes hook and loop fasteners (e.g., Velcro). For example, in some embodiments, the wristband 130 is an integrated Velcro strap. In other embodiments, other attachment means are used to secure the radial artery compression device 100 to the arm of the patient 50.

The substantially rigid frame 110 and the flexible sheet 120 may form the inflatable chamber 126. For example, the inner surface 113 of the frame 110 and the flexible sheet 120 may at least partially define the inflatable chamber 126. Stated differently, a wall of the inflatable chamber 126 may be defined by the frame 110. In this fashion, the inflatable chamber 126 may be defined by both a first portion (e.g., the substantially rigid frame 110) of the radial artery compression device 100 that does not change size or shape as the inflatable chamber 126 is inflated and a second portion (e.g., the flexible sheet 120) of the radial artery compression device 100 that does change in size or shape as the inflatable chamber 126 is inflated.

When the wristband 130 is secured to the wrist of the patient 50, the inflatable chamber 126 may be positioned adjacent to a radial artery 10 of the patient (see FIG. 5). In some embodiments, the radial artery compression device 100 includes only a single inflatable chamber 126. The use of the single inflatable chamber 126 may provide one or more advantages relative to radial artery compression devices that employ multiple inflatable chambers, such as ease of construction and/or ease of use. In some embodiments, the maximum capacity of the inflatable chamber is between 3 mL and 30 mL. For example, in some embodiments, the maximum capacity of the inflatable chamber 126 is between 3 mL and 12 mL, between 3 mL and 20 mL, between 3 mL and 25 mL, between 5 mL and 15 mL, between 10 mL and 20 mL, between 10 mL and 30 mL, or between 15 mL and 30 mL. The inflatable chamber 126 may be configured for applying varying amounts of pressure to a radial access site of the patient 50. In some embodiments, the inflatable chamber 126 provides pressure to the radial access site in a manner that avoids restricting the ulnar artery.

In some embodiments, the radial artery compression device 100 includes tubing 135 that extends from a first aperture 116 (see FIG. 5) in the substantially rigid frame 110 to a valve 140. The tubing 135 and the valve 140 may be in fluid communication with the inflatable chamber 126 that is formed by the substantially rigid frame 110 and the flexible sheet 120. In some embodiments, the valve 140 is configured to allow fluid to flow through the valve 140 when the valve 140 is coupled to an inflation device (e.g., a syringe), but prevents fluid flow through the valve 140 when the valve 140 is not coupled (i.e., detached from) the inflation device. In other words, the valve 140 may maintain a positive fluid pressure within the inflatable chamber 126 after the inflation device has been uncoupled from the valve 140.

In the depicted embodiment, the tubing 135 is coupled to the frame 110 via a connector 150 that protrudes from the outer surface 111 of the frame 110. In some embodiments, the tubing 135 extends from the connector 150 for a length of 5 cm to 15 cm, 6 cm to 15 cm, 8 cm to 15 cm, 10 cm to 15 cm, 12 cm to 15 cm, 6 cm to 12 cm, 6 cm to 10 cm, 6 cm to 8 cm, or 8 cm to 10 cm in length. In other words, in some embodiments, the tubing 135 is between about 5 cm to about 15 cm. In other embodiments, no tubing 135 is used. In other embodiments, the tubing 135 is of some other length.

In some embodiments, the radial artery compression device 100 may further include a retainer 160 (e.g., a clip) that is configured to secure a free end of the tubing 135 to the frame 110. In some embodiments, when the radial artery compression device 100 is secured to the right arm of the patient 50, the retainer 160 may be positioned (1) ulnar or radial of the connector 150 and/or (2) proximal or distal of the connector 150. For example, when the depicted embodiment is secured to the right arm of the patient 50 as shown in FIG. 1, the retainer 160 is positioned radial of and distal of the connector 150. The retainer 160 and the connector 150 may be positioned at a distance from one another such that, when a proximal end of the tubing 135 is attached to the retainer 160, only a small length of the tubing 135 protrudes from the radial artery compression device 100, thereby minimizing the bulk of the radial artery compression device 100.

Figure 6:
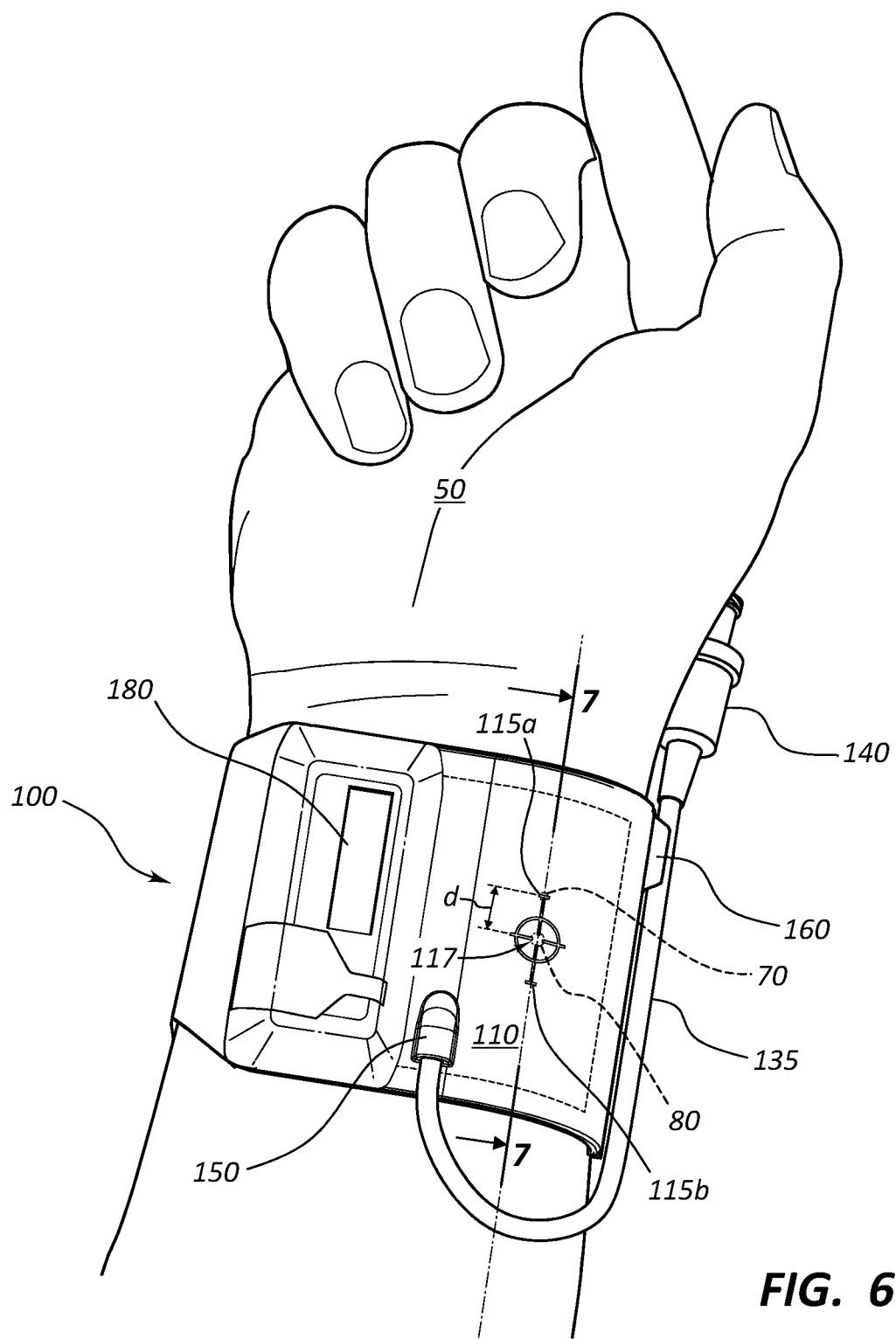
FIG. 6 is a perspective view of the radial artery compression device of FIGS. 1-5 showing the relative positioning of indicia to a puncture site and an arteriotomy site.
Figure 7:
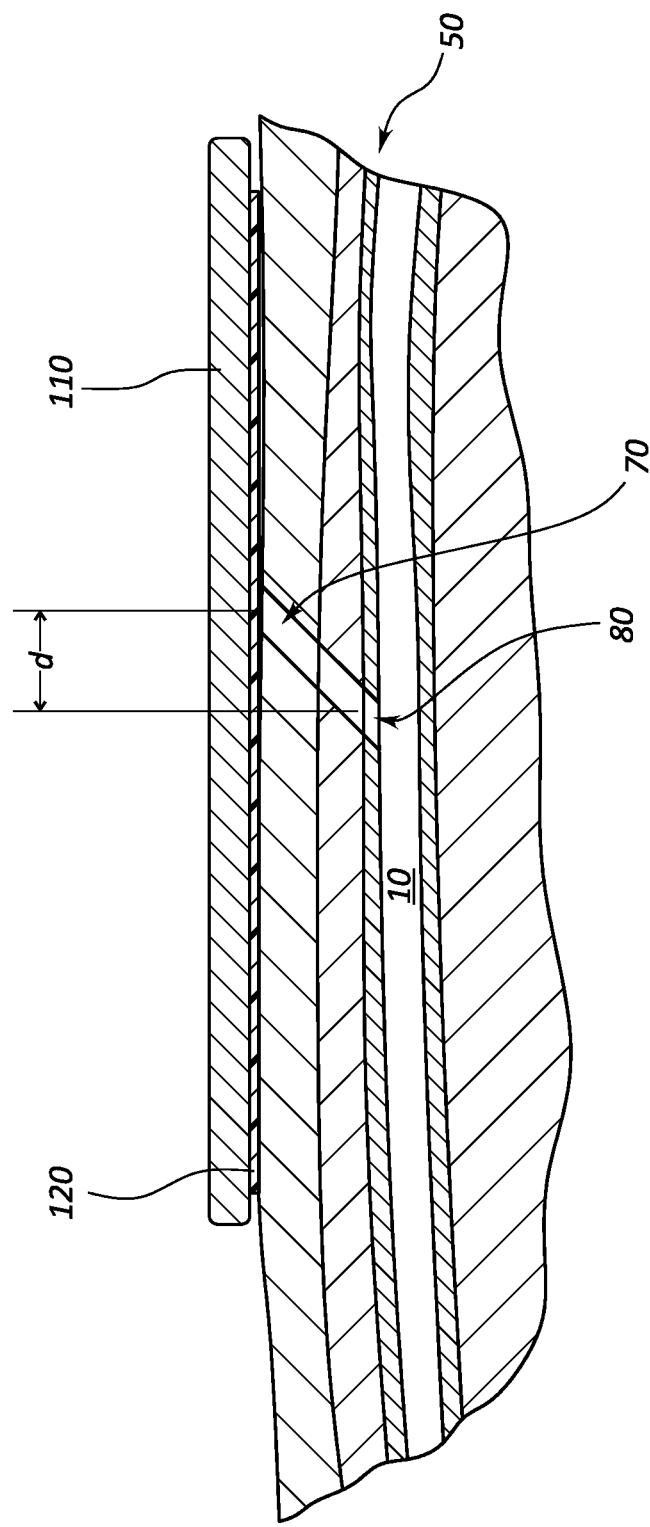
FIG. 7 is a cross-sectional view of the radial artery compression device of FIGS. 1-6 showing a puncture site and an arteriotomy site.

FIGS. 6 and 7 show one way of positioning the radial artery compression device 100 relative to a puncture site 70 and an arteriotomy site 80. More particularly, FIG. 6 shows the radial artery compression device 100 secured to the wrist of the patient 50 at a particular location relative to the puncture site 70, while FIG. 7 provides a cross-sectional view of the through plane 7-7 of FIG. 6.

When an elongate device, such as a needle, sheath, or catheter, is introduced into the radial artery 10 for an interventional procedure, the elongate device may be inserted at an angle such that the location where the elongate device passes through the skin (i.e., the puncture site) is not directly above the location where the elongate device passes through the artery wall (i.e., the arteriotomy site). In other words, the puncture site may be separated from the arteriotomy site by a distance (d). In some embodiments, the distance (d) is approximately 1-10 mm, 2-5 mm, and/or 3-4 mm.

In some circumstances, it may be advantageous to focus compression on the arteriotomy site 80 rather than the puncture site 70. In other words, hemostasis may be more rapidly and effectively achieved by applying a compression force to the arteriotomy site 80 in a relatively direct manner. To assist a practitioner in placing the radial artery compression device 100 at a location that provides appropriate compression to the arteriotomy site 80, the radial artery compression device 100 may include indicia on the frame 110. The indicia on the frame 110 may be designed to facilitate identification of the arteriotomy site 80 relative to the visible puncture site 70 in the skin of the patient 50.

For example, in the depicted embodiment, a first indicium 115a is disposed on the frame 110. In the depicted embodiment, the first indicium 115a is located at the intersection of a T-shaped mark on the frame 110. When the first indicium 115a is aligned with the puncture site 70 that is visible through the transparent frame 110 and the transparent flexible sheet 120, a second indicium 117 is disposed directly over the (non-visible) arteriotomy site 80. In the depicted embodiment, the second indicium 117 is the center of a target-shaped mark on the frame 110. In some embodiments, the second indicium 117 is disposed directly above a center of the flexible sheet 120. Stated differently, the second indicium 117 may be disposed directly over a region of the inflatable chamber 126 that is designed to extend furthest from the frame 110 when the inflatable chamber 126 is in an inflated state.

In some embodiments, the radial artery compression device 100 may additionally or alternatively include an indicium 115b. The indicium 115b may be aligned with a puncture site when the radial artery compression device 100 is placed on the left hand of the patient 50. Stated differently, in some embodiments, the radial artery compression device 100 may include indicia to facilitate alignment with the puncture site 70 regardless of the arm on which the radial artery compression device 100 is placed. One of ordinary skill in the art will recognize that indicia that differ in some ways from the indicia shown in FIG. 6 may be used for analogous purposes. In other words, various forms of indicia may be used to facilitate proper alignment of the radial artery compression device 100.

In some embodiments, the radial artery compression device 100 may include one or more of the following components: a pressure sensor, a timer, an alarm, a control unit, a power source, a wireless connection, and a display 180. In some embodiments, one or more of these components are enclosed within and/or supported by a housing 170. The housing 170 may be fixedly or detachably coupled to the frame 110. For example, in the depicted embodiment, the housing 170 is fixedly coupled to and extends from the frame 110. In embodiments in which the housing 170 is detachably coupled to the frame, the housing 170 and/or one or more components disposed therein (e.g., a pressure sensor, a timer, an alarm, a control unit, a power source, a wireless connection, or a display 180) may be reprocessed and/or refurbished for further use.

In some embodiments that include a pressure sensor or pressure transducer (not shown), the pressure sensor may be in fluid communication with the inflatable chamber 126. For example, the pressure sensor may be in fluid communication with the inflatable chamber 126 through a second aperture (not shown) in the substantially rigid frame 110. The pressure within the inflatable chamber 126, as measured by the pressure sensor, may inform protocols for use of the radial artery compression device 100. For example, pressure measurements obtained by the pressure sensor may be relayed to the display 180. The practitioner may use the pressure information on the display to increase or decrease the amount of fluid within the inflatable chamber 126 as desired. In some embodiments, the pressure sensor is detachable from the remaining portions of the radial artery compression device 100. In other embodiments, the pressure transducer is not detachable from the radial artery compression device 100.

As noted above, some radial artery compression devices include a timer. In some embodiments, the timer is a countdown timer. In other or further embodiments, the timer is a stopwatch (i.e., count-up) timer. The timer may be configured to measure time from some reference period, such as when an actuator (e.g., a button or pull tab) is actuated. In some embodiments, time is measured from when the radial artery compression device 100 is positioned on the arm of the patient 50 and initially inflated. The timer may additionally or alternatively measure time from when fluid is initially removed from the inflatable chamber 126 during deflation. In some embodiments, the timer may be configured to measure the amount of time that the inflatable chamber 126 has remained at a particular pressure.

In some instances, the timer may be in communication with the display 180. In some embodiments, the display 180 shows the amount of elapsed time in minutes and seconds. In other or further embodiments, the display may show the amount of elapsed time in hours and minutes. In some embodiments, the display may transition from displaying minutes and seconds to displaying hours and minutes once the amount of elapsed time reaches one hour. In some embodiments, the timer is detachable from the remaining portions of the radial artery compression device 100. In other embodiments, the timer is not detachable.

In some embodiments, the radial artery compression device 100 includes an alarm. In some cases, the alarm may be a visible alarm (e.g., the flashing of light-emitting diodes). In other or further embodiments, the alarm may be audible. The alarm may alert the patient 50 and/or the practitioner to certain information (e.g., the length of the time that the radial artery compression device 100 has remained in a particular state). Based on this information, the practitioner and/or the patient 50 may make any needed changes.

In some embodiments, the radial artery compression device 100 may include a wireless connection (e.g., via Bluetooth or Wi-Fi). Information from the radial artery compression device 100 (e.g., information relating to pressure or elapsed time) may be wirelessly transmitted to one of more other devices to alert a medical practitioner of treatment needs, such as the need to modify the amount of pressure provided to the radial artery at a particular time.

The radial artery compression device 100 may be used at or near the conclusion of a medical procedure to facilitate hemostasis of the radial artery 10. For example, in some procedures, the radial artery compression device 100 may be secured to the wrist of the patient 50, such as via the wristband 130. The practitioner may secure the radial artery compression device 100 to the wrist of the patient 50 such that the inflatable chamber 126 of the radial artery compression device 100 is positioned adjacent to a radial access site. For example, in some embodiments, the radial artery compression device 100 is placed on the wrist around a portion of an elongate medical instrument that accesses the radial artery of the patient 50 through a radial access site.

In some circumstances, the practitioner may align the first indicium 115*a* on the frame 110 of the radial artery compression device 100 with the puncture site 70 in the skin of the patient 50. For example, the practitioner may view the radial access site through the frame 110 and the flexible sheet 120 and align the first indicium 115*a* on the frame 110 with the puncture site 70. When the first indicium 115*a* is aligned with the puncture site 70, the inflatable chamber 126 of the radial artery compression device 100 may be positioned to provide compression to the arteriotomy site 80 that is upstream of the puncture site 70. Stated differently, when the first indicium 115*a* of the radial artery compression device 100 is aligned with the puncture site 70 in the skin of the patient 50, the inflatable chamber 126 may be positioned directly over an arteriotomy site of the patient 50. In some embodiments, the second indicium 117 is disposed directly over the arteriotomy site 80 when the first indicium 115*a* is aligned with the puncture site 70.

Once the radial artery compression device 100 is properly placed on the arm of the patient 50, the inflatable chamber 126 may be inflated in any suitable manner. For example, in some embodiments, the practitioner may connect an inflation device (e.g., a syringe) to the valve 140. Connecting the inflation device to the valve 140 may open the valve 140, allowing the practitioner to deliver fluid into the inflatable chamber 126. For example, a practitioner may advance a plunger of a syringe that is connected to the valve 140, causing fluid to pass through the valve 140, the tubing 135, and the first aperture 116 to enter into the inflatable chamber 126. The delivery of fluid to the inflatable chamber 126 may cause the inflatable chamber 126 to expand, thereby increasing the amount of pressure that is applied to the radial access site. Stated differently, inflating the inflatable chamber 126 may increase pressure that is applied to the radial access site.

In some circumstances, the inflatable chamber 126 may first be partially inflated to provide some compression force to the radial access site. With the inflatable chamber 126 in a partially inflated state, an elongate medical device that is partially inserted into the radial artery may be withdrawn from the radial artery such that no medical device extends through the puncture site 70 of the skin of the patient 50 to the arteriotomy site 80.

After the elongate medical device has been removed, fluid may then be delivered to the inflatable chamber 126 in an amount that is sufficient to stop bleeding at the arteriotomy site 80. For example, in some embodiments, sufficient fluid may be provided to fully inflate the inflatable chamber 126. Once enough fluid has been delivered to the inflatable chamber 126 to stop the bleeding, fluid within the inflatable chamber 126 may be slowly withdrawn until a flash of blood is visible at the skin puncture site 70 through the frame 110 and the flexible sheet 120. At this stage, additional fluid (e.g., 1-2 mL) may be injected back into the inflatable chamber 126 to stop the bleeding. This process may provide adequate pressure to achieve hemostasis while maintaining patency of the radial artery 10. In other words, this protocol can be used to ensure that sufficient pressure is provided to prevent bleeding, while avoiding the application of excessive force (which can unduly restrict blood flow through the radial artery 10).

As the arteriotomy site 80 and/or the puncture site 70 begin to heal, the amount of compression needed to maintain hemostasis may decrease. Accordingly, the practitioner may deflate the inflatable chamber 126 over a series of stages. Such deflation may follow a particular predetermined protocol. For example, in some embodiments, after the radial artery compression device 100 has been used to apply a compressive force for some period of time (e.g., 5 minutes to 5 hours), a predetermined volume (e.g., 0.5 mL to 3 mL) of fluid may be removed every 2-3 minutes until all of the air is removed. Provided that the removal of compression force does not result in further bleeding, the radial artery compression device 100 may then be removed from the patient 50. In other words, once compression is no longer needed to ensure hemostasis, the radial artery compression device 100 may be removed from the patient 50.

In some instances, fluid may be removed from the inflatable chamber 126 based on information provided by the radial artery compression device 100. For example, in some embodiments, the inflatable chamber 126 may be deflated based on information obtained from a timer or an alarm of the radial artery compression device 100. For example, the radial artery compression device may count the amount of time that has elapsed since the radial artery compression device 100 was placed on the patient 50 and alert the practitioner of the proper time to begin removing fluid from the inflatable chamber 126. The timer may be activated by an actuator, such as a button or a pull tab. In some embodiments, the timer may count up. In other or further embodiments, the timer may count down. The radial artery compression device 100 may also indicate the timing for staged deflation. In some instances, the practitioner or the patient 50 is alerted to the need to remove fluid based on a visible indicator (e.g., information provided on the display 180). The information from the visible indicator may be provided on the display 180, via lights (e.g., light-emitting diodes), or in some other manner. In other or further embodiments, the practitioner or the patient 50 is alerted to the need to remove fluid based on one or more sounds (e.g., the sounds of an audible alarm) that are emitted from the radial artery compression device 100. In some embodiments, lights (e.g., LEDs) or other indicia inform the practitioner of the stage of deflation. For example, in some embodiments, lights may be used to indicate the number of times fluid has been removed from the inflatable chamber 126.

Figure 8:
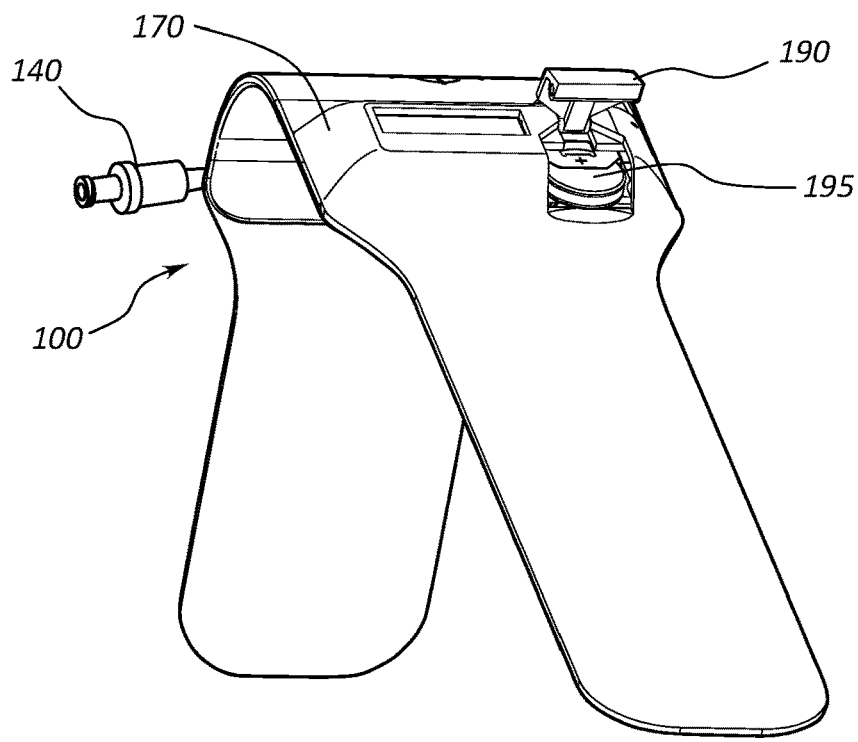
FIG. 8 is a perspective view of the radial artery compression device of FIGS. 1-7 showing a battery removal mechanism.

The radial artery compression device 100 may be powered by any suitable power source. For example, in the embodiment depicted in FIGS. 1-8, the radial artery compression device 100 includes a battery 195 that is disposed within the housing 170. The battery 195 may provide power to a pressure sensor, a timer, an alarm, and/or the display 180. In some embodiments, the radial artery compression device 100 is configured to facilitate removal of the battery from the housing. For example, the radial artery compression device 100 may include a battery latch 190 that is rotatably coupled to the housing 170. The battery latch 190 may be opened as shown in FIG. 8 to remove the battery 195 from the radial artery compression device 100. In other words, the radial artery compression device 100 may be configured to facilitate removal of one or more batteries 195 for the housing 170. Facile removal of the battery 195 may allow the radial artery compression device 100 to be discarded separate from battery waste.

Figure 9:
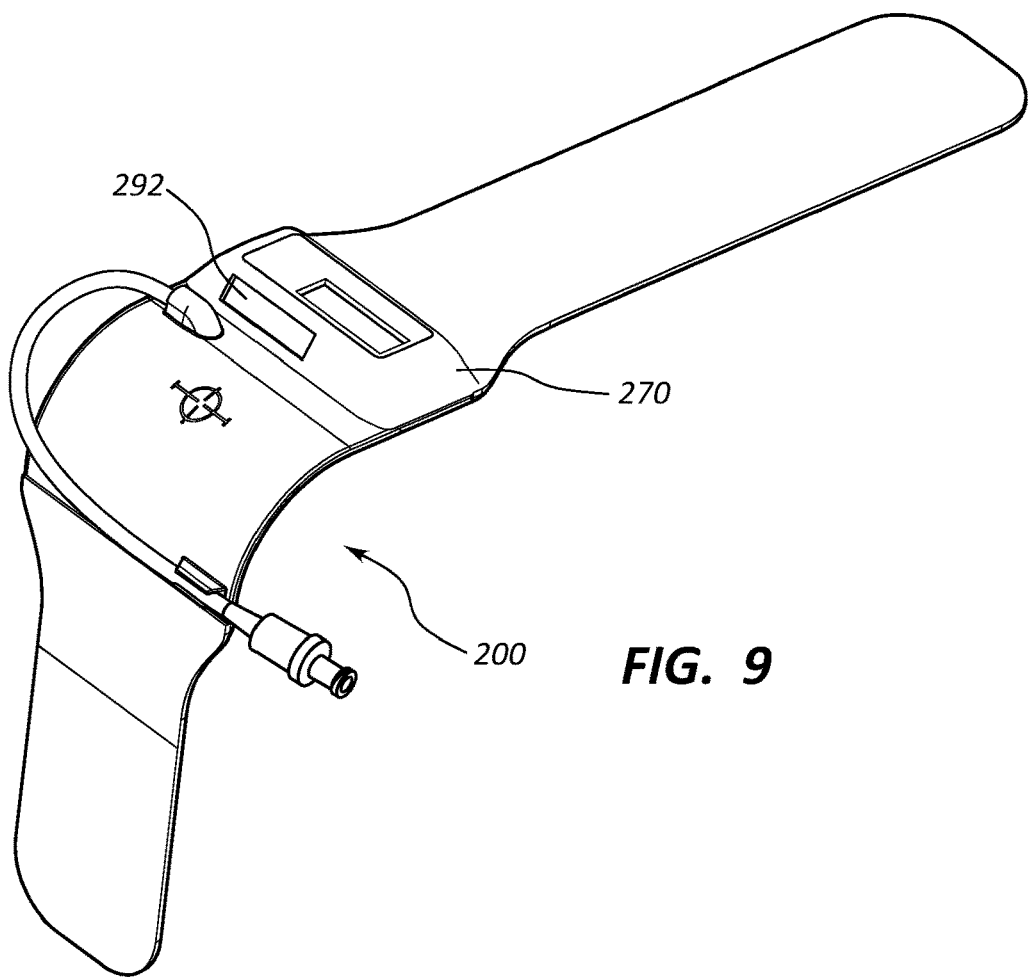
FIG. 9 is a perspective view of a solar-powered radial artery compression device.

Radial artery compression devices need not be powered by one or more batteries. For example, FIG. 9 provides a perspective view of a radial artery compression device 200 that includes a solar panel 292 that is supported by a housing 270. The radial artery compression device 200 may use solar energy to power components such as a pressure sensor, a timer, an alarm, lights, and/or a display. Alternatively, some radial artery compression devices may be powered by a slow-discharge capacitor. The use of a slow-discharge capacitor may allow the radial artery compression device to be discarded without concern for battery waste. In still other embodiments (e.g., embodiments lacking components such as a pressure sensor, a timer, an alarm, lights, and a display), the radial artery compression device may not include a power source within the housing.

Figure 10:
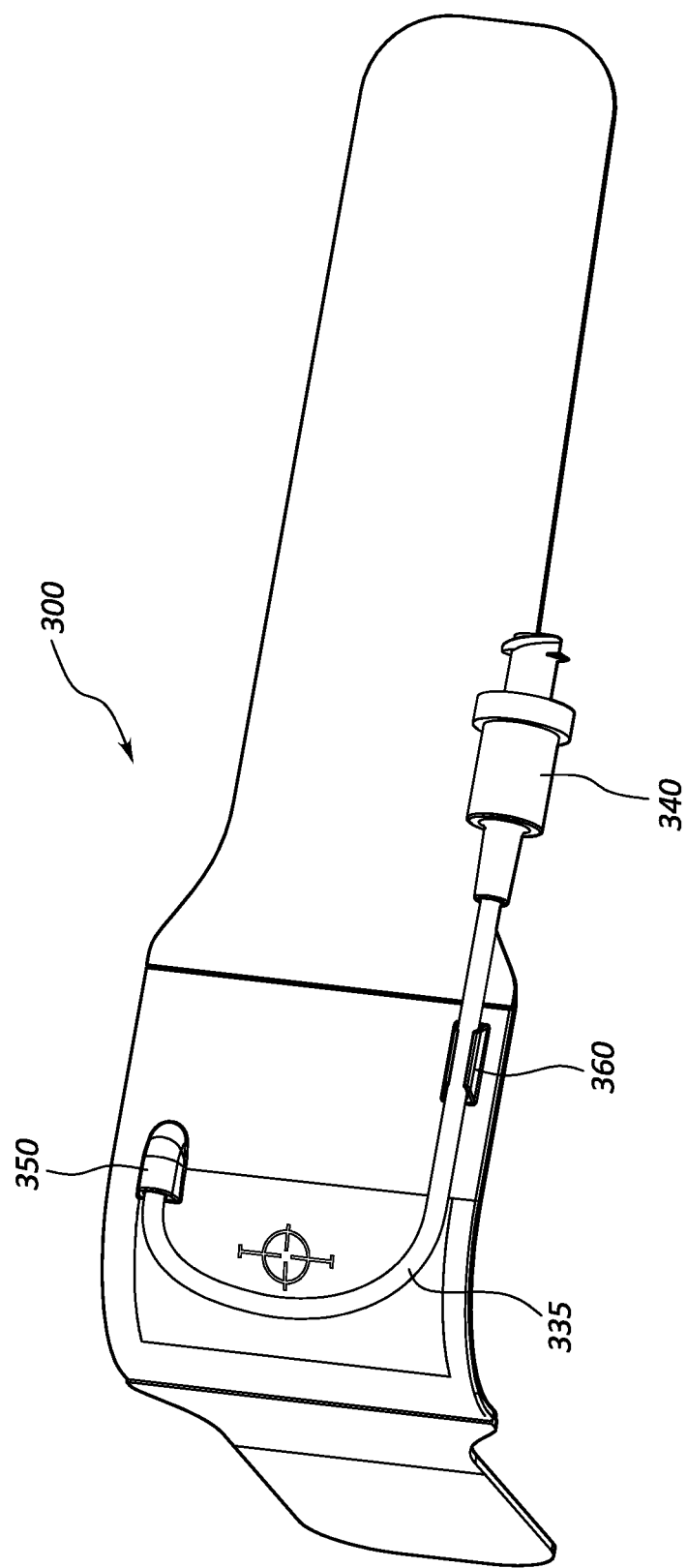
FIG. 10 is a perspective view of another embodiment of a radial artery compression device.

FIG. 10 provides a perspective view of another radial artery compression device 300. The radial artery compression device 300 is generally analogous to the radial artery compression devices 100, 200 described above. However, in the embodiment shown in FIG. 10, the connector 350 and the retainer 360 are positioned in different locations when compared to the connectors and retainers shown in FIGS. 1-9.

When the radial artery compression device 300 is disposed on the right wrist of a patient for placement over a radial artery, the connector 350 is both proximal and radial of the retainer 360. Tubing 335 may initially extend radially from the connector 350 and then bend such that a valve 340 at the free end of the tubing is disposed ulnar of the connector 350. The retainer 360 may secure the tubing 335 adjacent to the remaining portions of the radial artery compression device 300.

Some radial artery compression devices described herein, such as radial artery compression devices 100, 200, and 300 may be placed on either arm of the patient 50. For example, while the radial artery compression device 100 is shown in FIG. 1 on the right arm of the patient 50, the radial artery compression device 100 may alternatively be used on the left arm of the patient 50. When the radial artery compression device 100 is disposed on the left arm of the patient 50, the frame 110 may be contoured to curve around a thumb-side portion of the left wrist of the patient 50. Stated differently, when the radial artery compression device 100 of FIG. 1 is properly placed on the left arm of the patient 50, the radial artery compression device 100 of FIGS. 1-8 may be rotated such that the connector 150 is both ulnar of and distal of the retainer 160.

While the compression devices described above are described as radial artery compression devices, some compression devices may, additionally or alternatively, be suitable for compression of an ulnar artery. For example, a compression device may be placed on the patient such that the frame curves around the ulnar side of the wrist. When placed on the patient in this manner, the inflatable chamber may be positioned adjacent to the ulnar artery such that inflation of the inflatable chamber applies pressure to an access site in the ulnar artery. Thus, some compression devices described herein may be used to promote healing at access sites in an ulnar artery.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A radial artery compression device, the device comprising:
   a substantially rigid frame, the frame comprising an outer surface and an inner surface, wherein at least a portion of the frame is transparent;
   a flexible sheet that is coupled to the frame, wherein at least a portion of the sheet is transparent;
   an inflatable chamber that is at least partially defined by the inner surface of the frame and the flexible sheet;
   a first indicium positioned directly on the frame; and
   a second indicium positioned directly on the frame, wherein the second indicium is axially offset from the first indicium.

2. The radial artery compression device of claim 1, wherein the flexible sheet comprises a peripheral portion that is attached to the frame and a central portion that is not attached to the frame.

3. The radial artery compression device of claim 1, further comprising a wristband that is configured to secure the frame to a wrist of a patient such that the inflatable chamber is positioned adjacent to a radial artery.

4. The radial artery compression device of claim 1, wherein the frame is contoured to curve around a thumb-side portion of a wrist.

5. The radial artery compression device of claim 1, further comprising a valve that is in fluid communication with the inflatable chamber.

6. The radial artery compression device of claim 5, wherein the valve is configured to (1) allow fluid to flow through the valve when the valve is coupled to an inflation device and (2) prevent fluid flow through the valve when the valve is not coupled to the inflation device.

7. The radial artery compression device of claim 5, wherein the valve is in fluid communication with the inflation chamber via tubing that extends from a first aperture in the frame to the valve.

8. The radial artery compression device of claim 7, wherein the tubing is coupled to the frame via a connector that protrudes from the outer surface of the frame.

9. The radial artery compression device of claim 8, further comprising a retainer that is configured to secure a free end of the tubing to the frame.

10. The radial artery compression device of claim 9, wherein the retainer is positioned both (1) ulnar or radial of and (2) either proximal or distal of the connector when the radial artery compression device is coupled to the wrist of the patient.

11. The radial artery compression device of claim 1, further comprising a timer.

12. The radial artery compression device of claim 1, further comprising a pressure sensor that is in fluid communication with the inflatable chamber.

13. The radial artery compression device of claim 1, wherein the first indicium and the second indicium are designed to facilitate identification of an arteriotomy site relative to a skin puncture site.

14. The radial artery compression device of claim 1, wherein the second indicium is axially offset from the first indicium by a distance ranging from about 1 mm to about 10 mm.

15. The radial artery compression device of claim 1, wherein the second indicium is axially offset from the first indicium by a distance ranging from about 3 mm to about 4 mm.

16. A radial artery compression device comprising:
a substantially rigid frame;
a wristband for securing the substantially rigid frame adjacent to a wrist of a patient;
an inflatable chamber for applying pressure to a radial access site of a patient;
a first indicium disposed directly on the substantially rigid frame; and
a second indicium disposed directly on the substantially rigid frame, wherein the second indicium is axially offset from the first indicium;
wherein at least a portion of the substantially rigid frame and at least a portion of the inflatable chamber are transparent;
wherein the radial artery compression device is configured such that alignment of the first indicium with a puncture site in a patient's skin positions the second indicium and the inflatable chamber directly over an arteriotomy site of the patient, and
wherein the arteriotomy site is located offset from the puncture site.

17. The radial artery compression device of claim 16, wherein a wall of the inflatable chamber is defined by the frame.

* * * * *